United States Patent
Grunhut et al.

(10) Patent No.: US 7,976,499 B2
(45) Date of Patent: Jul. 12, 2011

(54) AUTOMATIC INJECTION DEVICE

(75) Inventors: Guillaume Grunhut, Grenoble (FR); Lionel Maritan, Pierre Chatel (FR); Frederic Perot, Saint Paul de Varces (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 101 days.

(21) Appl. No.: 12/296,730

(22) PCT Filed: Apr. 11, 2007

(86) PCT No.: PCT/IB2007/002016
§ 371 (c)(1),
(2), (4) Date: May 5, 2009

(87) PCT Pub. No.: WO2007/132353
PCT Pub. Date: Nov. 22, 2007

(65) Prior Publication Data
US 2009/0312705 A1    Dec. 17, 2009

(30) Foreign Application Priority Data

Apr. 11, 2006  (FR) ..................... 06 03200

(51) Int. Cl.
*A61M 5/00* (2006.01)
*A61M 37/00* (2006.01)
*A61M 31/00* (2006.01)
(52) U.S. Cl. ................. 604/110; 604/506; 604/135
(58) Field of Classification Search ............. 604/110, 604/117
See application file for complete search history.

(56) References Cited

U.S. PATENT DOCUMENTS

| | | | |
|---|---|---|---|
| 3,370,588 A | 2/1968 | Burke | |
| 4,964,866 A | 10/1990 | Szwarc | |
| 4,986,818 A | 1/1991 | Imbert et al. | |
| 5,092,842 A * | 3/1992 | Bechtold et al. | 604/135 |
| 5,137,516 A | 8/1992 | Rand et al. | |

(Continued)

FOREIGN PATENT DOCUMENTS

EP        0229204        7/1987

(Continued)

*Primary Examiner* — Nicholas D Lucchesi
*Assistant Examiner* — Ian K Holloway
(74) *Attorney, Agent, or Firm* — David M. Fortunato; Roylance, Abrams, Berdo and Goodman LLP

(57) ABSTRACT

The present invention relates to a device (1) for automatic injection of a product (3) and a needle (6). The device comprises:—a housing (8) for the container (5), the container being movable relative to the housing between an initial position, in which a tip of the needle does not extend beyond a distal end of the housing and in which the container is in one of a passive state and an active state, to an insertion position, distally spaced relative to the initial position and in which the tip of the needle extends beyond the distal end of the housing, movement of the container out of its first position being prevented when the container is in its passive state, and being permitted when the container is in its active state, and—a safety shield (10) coupled to the housing (8) for movement between a first position and a second position in which the tip of the needle does not extend beyond a distal end of the shield—a needle shield (2) coupled with said housing and covering the needle prior to use of said device, removal of said needle shield being with limited or no rotation of said needle shield.

25 Claims, 13 Drawing Sheets

U.S. PATENT DOCUMENTS

Figure 1:
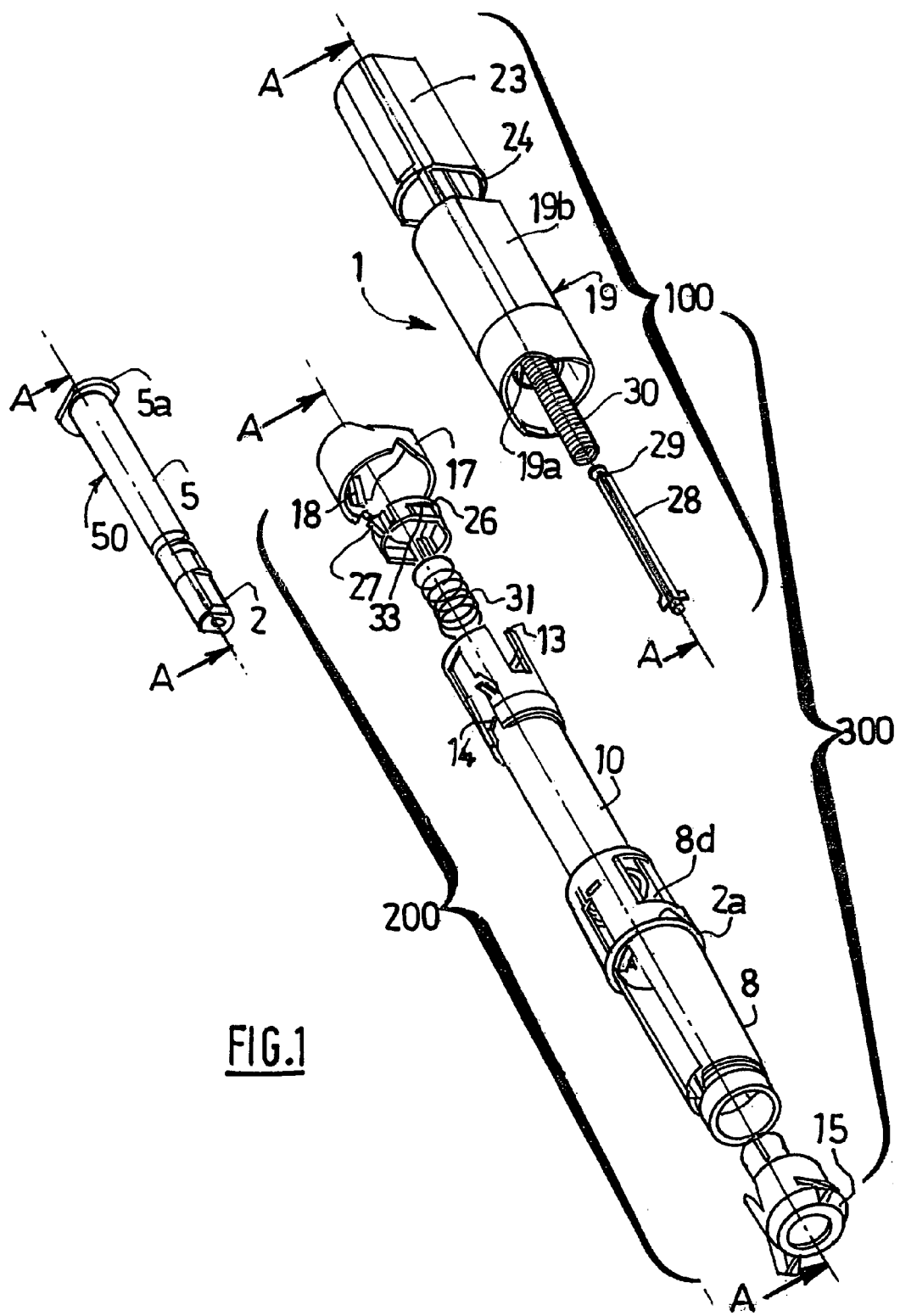

| | | | |
|---|---|---|---|
| 5,244,465 A * | 9/1993 | Michel | 604/208 |
| 5,540,664 A | 7/1996 | Wyrick | |
| 6,270,479 B1 * | 8/2001 | Bergens et al. | 604/156 |
| 6,503,230 B2 | 1/2003 | Odell et al. | |
| 6,585,702 B1 | 7/2003 | Brunel | |
| 6,623,459 B1 | 9/2003 | Doyle | |
| 6,719,732 B2 | 4/2004 | Courteix | |
| 6,805,686 B1 | 10/2004 | Fathallah et al. | |
| 6,979,316 B1 | 12/2005 | Rubin et al. | |
| 7,229,432 B2 | 6/2007 | Marshall et al. | |
| 7,297,136 B2 | 11/2007 | Wyrick | |
| 7,370,759 B2 | 5/2008 | Hommann | |
| 7,442,185 B2 | 10/2008 | Amark et al. | |
| 7,553,293 B2 | 6/2009 | Jensen et al. | |
| 7,658,724 B2 | 2/2010 | Rubin et al. | |
| 7,708,732 B2 * | 5/2010 | Norrie et al. | 604/506 |
| 7,717,877 B2 | 5/2010 | Lavi et al. | |
| 7,785,292 B2 | 8/2010 | Harrison | |
| 2003/0105430 A1 | 6/2003 | Lavi et al. | |
| 2005/0101919 A1 | 5/2005 | Brunnberg | |
| 2005/0165360 A1 | 7/2005 | Stamp | |
| 2005/0171483 A1 | 8/2005 | Williams | |
| 2005/0222539 A1 | 10/2005 | Gonzales et al. | |
| 2006/0173408 A1 * | 8/2006 | Wyrick | 604/110 |
| 2006/0184134 A1 | 8/2006 | Heiniger et al. | |
| 2006/0189938 A1 | 8/2006 | Hommann et al. | |
| 2006/0224124 A1 | 10/2006 | Scherer | |
| 2006/0264830 A1 | 11/2006 | Hommann | |
| 2006/0270984 A1 | 11/2006 | Hommann | |
| 2006/0270986 A1 | 11/2006 | Hommann et al. | |
| 2007/0021720 A1 | 1/2007 | Guillermo | |
| 2007/0027430 A1 | 2/2007 | Hommann | |
| 2007/0078382 A1 | 4/2007 | Hommann et al. | |
| 2007/0112310 A1 | 5/2007 | Lavi et al. | |
| 2007/0118081 A1 | 5/2007 | Daily et al. | |
| 2007/0129686 A1 | 6/2007 | Daily et al. | |
| 2007/0135767 A1 | 6/2007 | Gillespie, III et al. | |
| 2007/0142787 A1 | 6/2007 | Scherer | |
| 2007/0173770 A1 | 7/2007 | Stamp | |
| 2008/0039789 A1 | 2/2008 | Wyrick | |
| 2008/0132838 A1 | 6/2008 | Wyrick | |
| 2008/0147006 A1 | 6/2008 | Brunnberg et al. | |
| 2008/0154200 A1 | 6/2008 | Lesch | |
| 2008/0228143 A1 | 9/2008 | Stamp | |
| 2008/0228147 A1 | 9/2008 | David-Hegerich et al. | |
| 2008/0312590 A1 | 12/2008 | Barrow-Williams et al. | |
| 2008/0312591 A1 | 12/2008 | Harrison | |
| 2008/0312592 A1 | 12/2008 | Barrow-Williams et al. | |
| 2008/0312606 A1 | 12/2008 | Harrison et al. | |
| 2009/0012470 A1 | 1/2009 | Barrow-Williams | |
| 2009/0012471 A1 | 1/2009 | Harrison | |
| 2009/0054849 A1 | 2/2009 | Burnell et al. | |
| 2009/0105615 A1 * | 4/2009 | Kojima et al. | 600/583 |
| 2009/0124981 A1 | 5/2009 | Evans | |
| 2009/0270804 A1 | 10/2009 | Mesa et al. | |
| 2009/0281496 A1 | 11/2009 | Matusch | |
| 2010/0010453 A1 | 1/2010 | Riemelmoser | |
| 2010/0016793 A1 | 1/2010 | Jennings et al. | |
| 2010/0016794 A1 | 1/2010 | Corrigan | |
| 2010/0016795 A1 | 1/2010 | McLoughlin | |
| 2010/0036318 A1 | 2/2010 | Raday et al. | |
| 2010/0049140 A1 * | 2/2010 | Marsh et al. | 604/191 |
| 2010/0152659 A1 | 6/2010 | Streit et al. | |

FOREIGN PATENT DOCUMENTS

| | | |
|---|---|---|
| EP | 0592814 | 4/1994 |
| GB | 2414398 | 11/2005 |
| GB | 2451662 | 11/2009 |
| GB | 2451665 | 11/2009 |
| WO | WO03013632 | 2/2003 |
| WO | WO03099358 | 12/2003 |
| WO | WO2005044348 | 5/2005 |

* cited by examiner

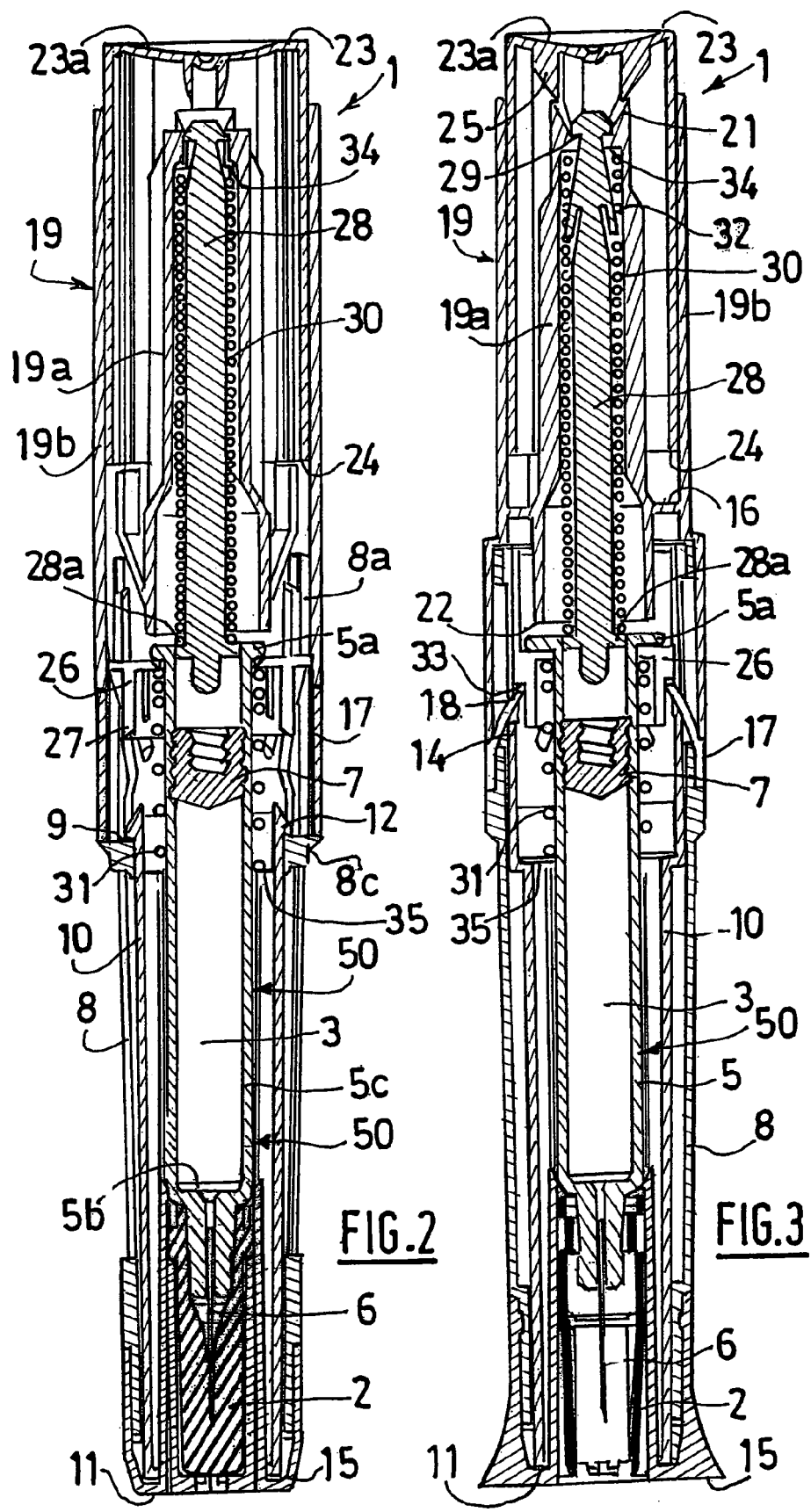

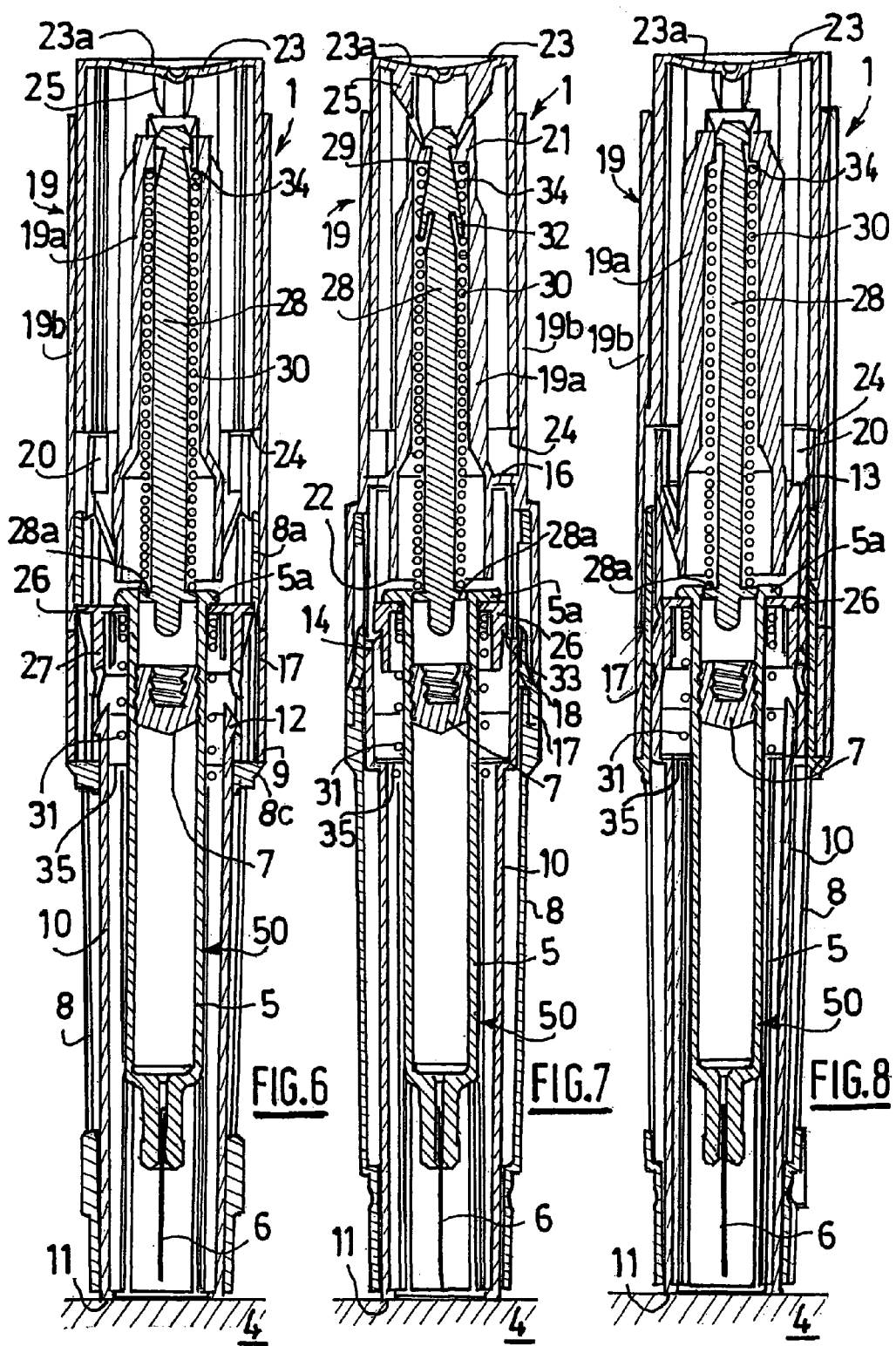

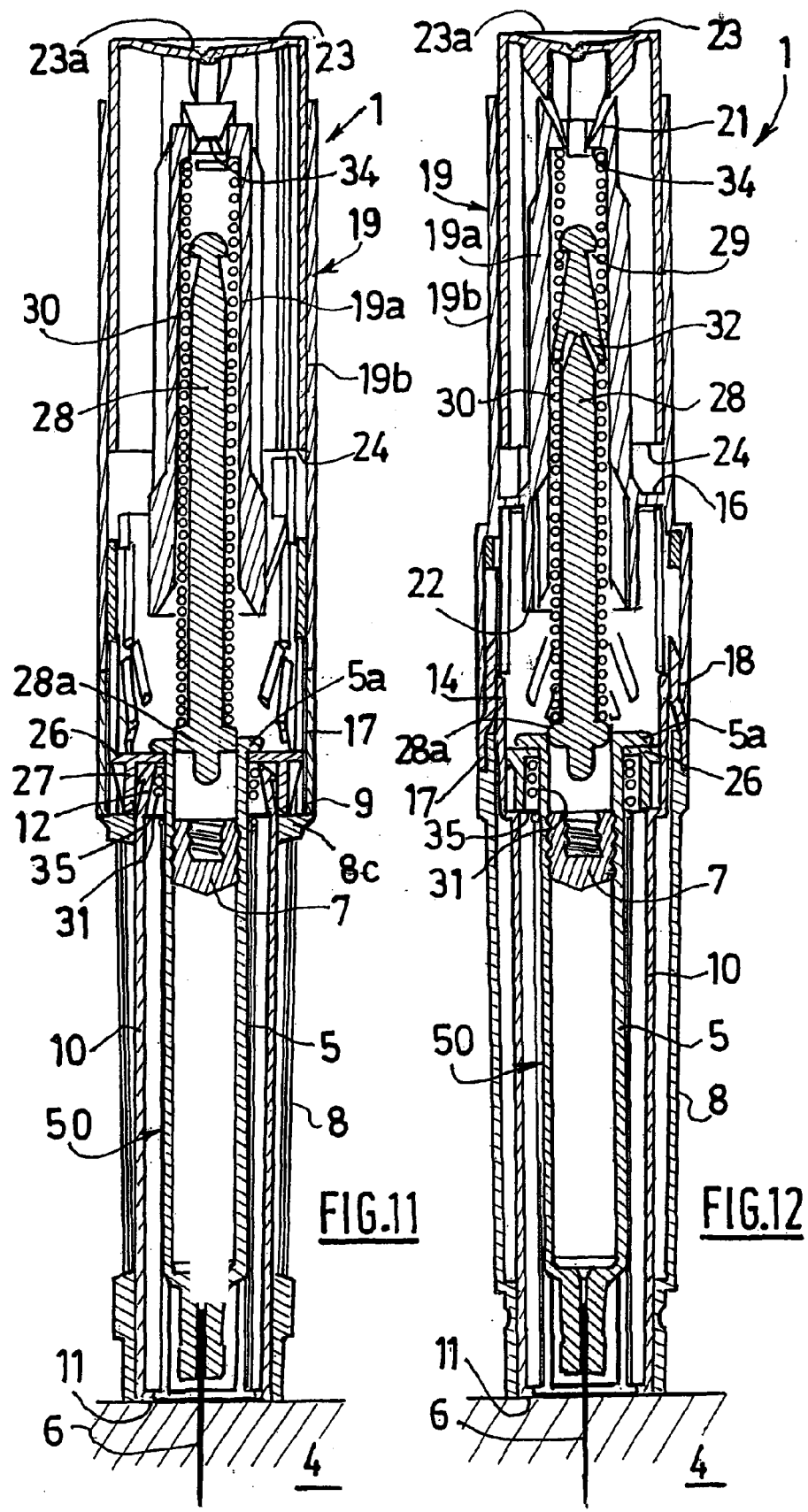

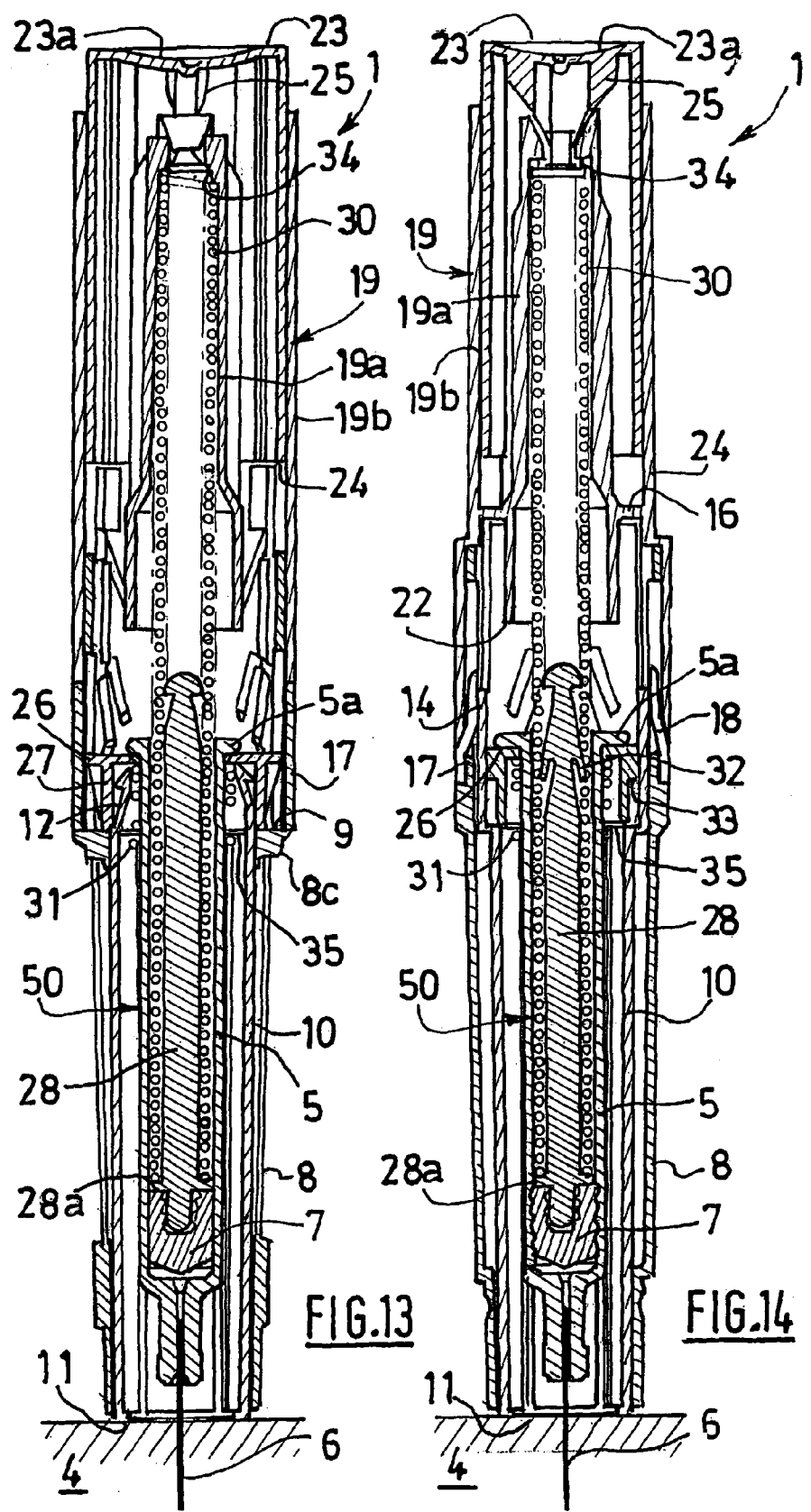

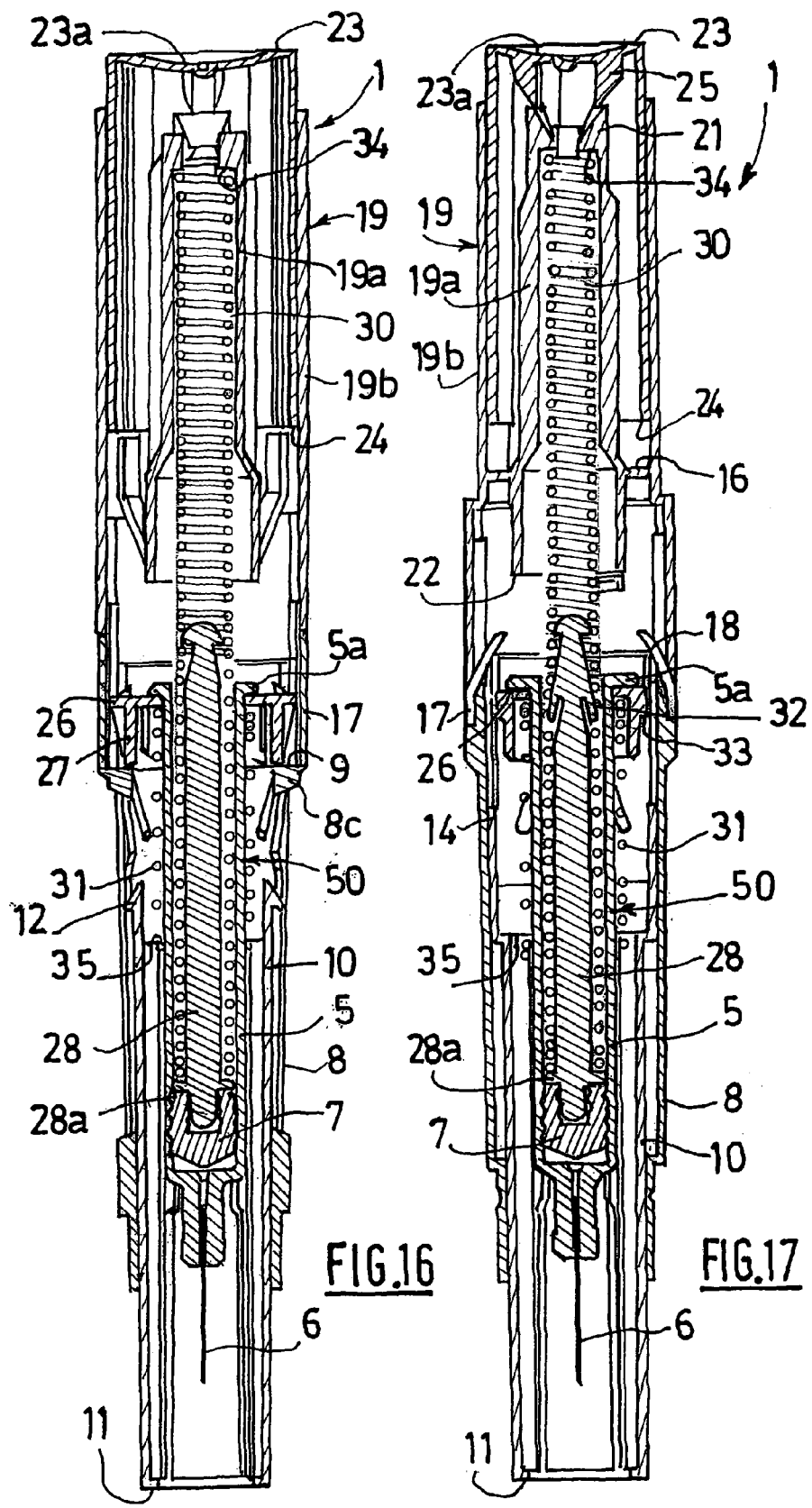

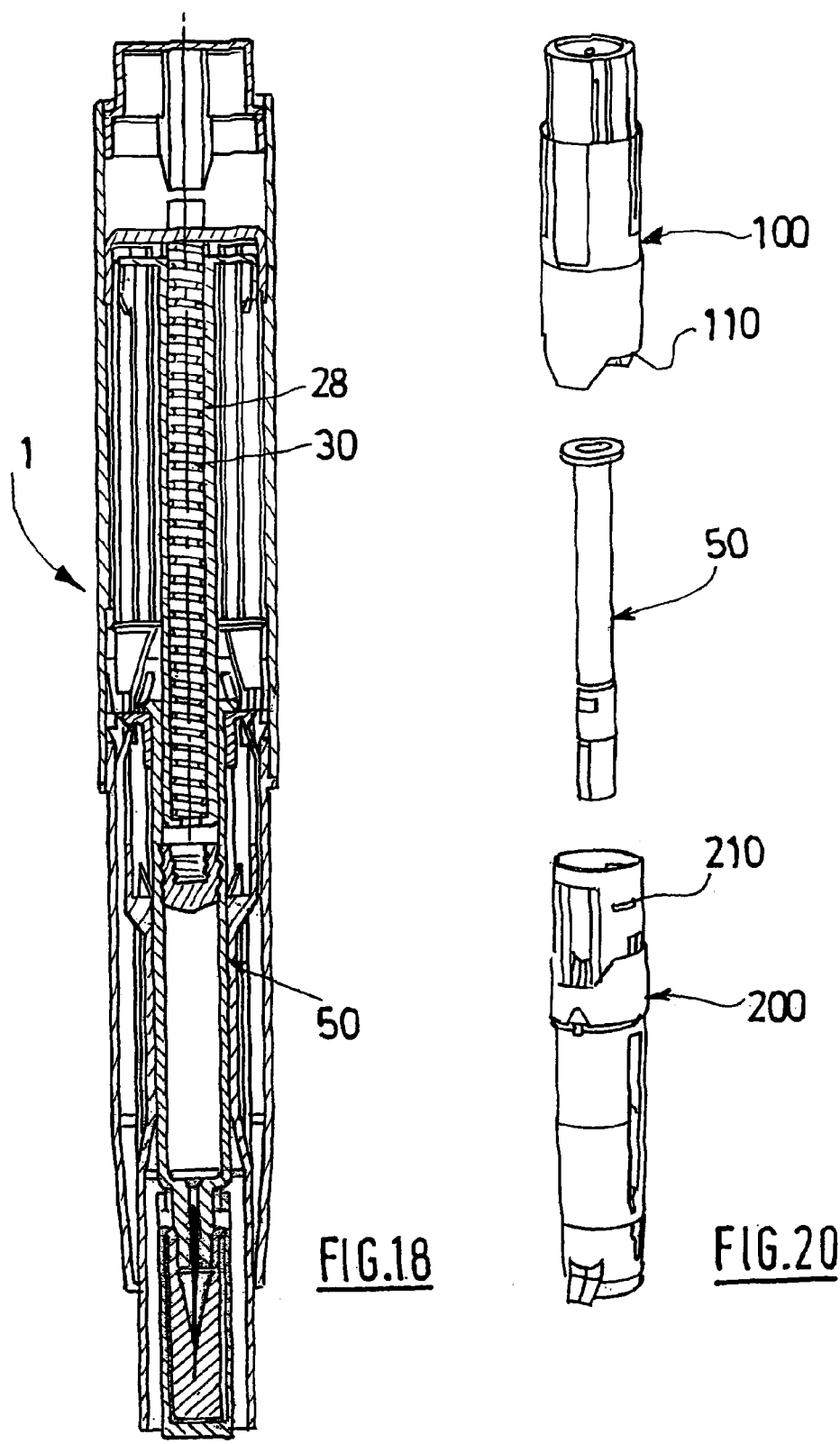

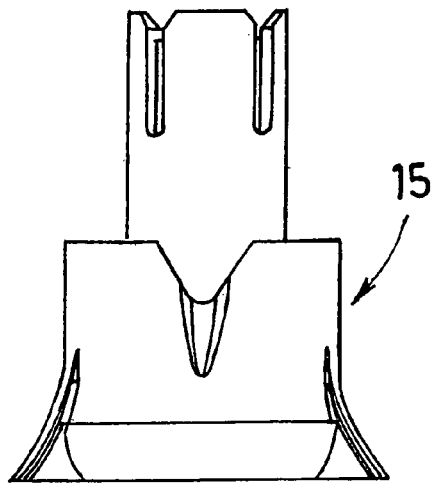
FIG.19a
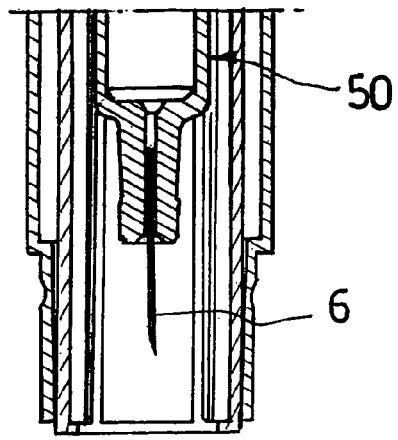
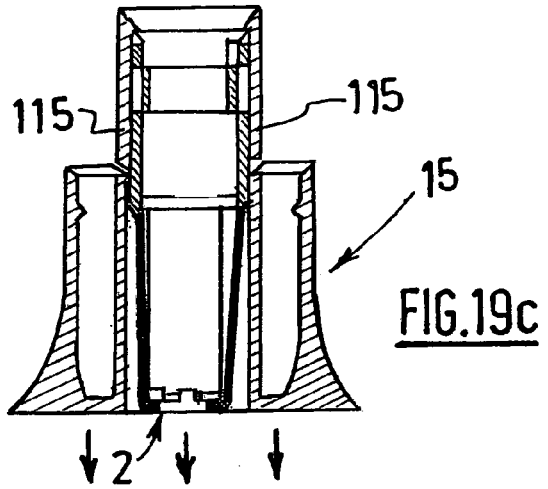
FIG.19c
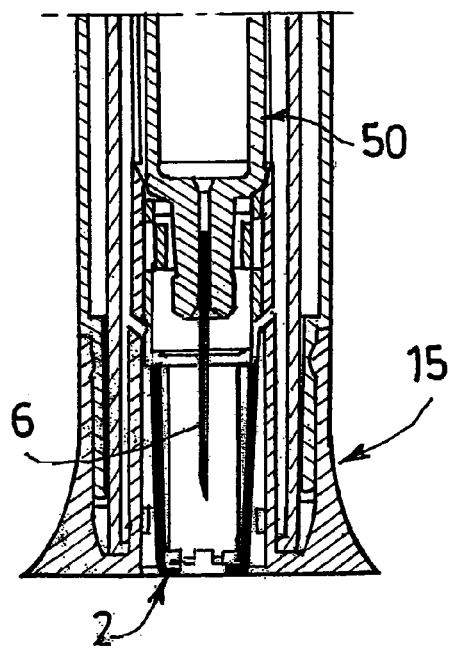
FIG.19b
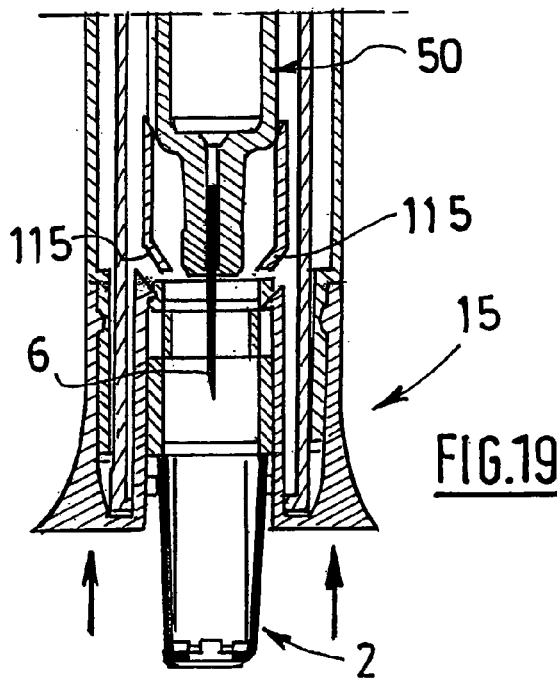
FIG.19d

AUTOMATIC INJECTION DEVICE

The present invention relates to a device for automatic injection of a product in a very safe way, especially for self-injection.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must be deactivated after use before it is disposed of. Preferably, the needle should not be exposed, before and after use, in order to prevent any accidental needlestick injury.

The injection devices of the prior art are usually provided with needle shields that are made of rubber or elastomeric material. A drawback of these devices is that the sharp needle, embedded into the rubber shield may create a core of rubber if rotated when removed. Then, this rubber core, located into the needle internal diameter may then block the needle and prevent the drug to be injected or may be injected into the patient's skin together with the drug upon activation of the injection device.

It would therefore be of interest to provide an injection device having an appropriate needle shield that does not jeopardize the quality of the injection when it is removed from the injection device before use.

Another important requirement of these self-injection devices is that they must not be able to be activated inadvertently, before the patient is ready to perform the injection, and in particular before the device is correctly applied at the right injection site.

Such self-injectors with automatic insertion and injection steps have been described in document WO2005/044348. The device described in WO2005/044348 comprises numerous complex elements and it is difficult to manufacture. Moreover, although the device described in this document comprises some safety means in order to cover the needle after use, this safety means are triggered by removal of the device from the injection site but only if the totality of the product has been injected.

In some cases though, the user may withdraw the self-injection device before the injection is completed. It is then of utmost importance that, in such a case, the safety be immediately triggered, although the injection is not completed. Otherwise, the patient may hurt himself or herself by accidental pricking or worse, he or she may reinsert the needle at a second injection site, and realize an inappropriate injection of the rest of the product.

Moreover, it is also important that the user be informed that the totality of the product has been injected and that he may withdraw the device from the injection site.

In consequence, there is a need for self-injection devices that would be easy to manufacture and assemble and for which the safety means would be automatically triggered by removal of the device from the injection site, even if the totality of the product has not been yet injected, and in which the needle would be efficiently protected before use by an appropriate needle shield, the removal of which would not jeopardize the quality of the injection to come.

There is also a need for such a self-injection device that would clearly indicate to the user that the injection is completed.

The present invention meets this need by proposing a device for automatic injection of a product into an injection site, said device comprising safety means automatically triggered by removal of the device from the injection site, even if the injection is not completed, said device also comprising a needle shield for protecting the needle before use of the device, the removal of said needle shield having no impact on the quality of the injection.

The present invention relates to a device for automatic injection of a product into an injection site, the product being carried by a container having an open proximal end and a substantially closed distal end and having a reservoir defined therebetween, and a needle provided at the distal end and in fluid communication with the reservoir to provide an outlet port for the product from the container, and a piston provided in the container and movable with respect with the container, the movement of the piston causing the product to be expelled from the container through the needle, characterized in that said device comprises:

- a housing for the container, the container being movable relative to said housing between an initial position, in which a tip of the needle does not extend beyond a distal end of said housing and in which the container is in one of a passive state and an active state, to an insertion position, distally spaced relative to said initial position and in which the tip of the needle extends beyond said distal end of said housing, movement of the container out of its initial position being prevented when the container is in its passive state, and being permitted when the container is in its active state, and
- a safety shield coupled to said housing for movement between a first position and a second position in which the tip of the needle does not extend beyond a distal end of said safety shield, movement of said safety shield out of its first position placing the container in its active state, said safety shield being movable to its second position when the container is in said insertion position, said safety shield being secured against proximal movement when in said second position,
- a needle shield coupled with said housing and covering the needle prior to use of said device, removal of said needle shield from the device being with limited or no rotation of said needle shield.

In the injection device of the invention, the generation of contaminating particles or dust in the area of the needle shield, before the needle shield is removed and at the time the needle shield is removed from the injection device, is avoided.

In an embodiment of the invention, said needle shield and said housing are provided with guiding means designed to allow the longitudinal translation of the needle shield with respect to said housing while preventing its rotation, when said needle shield is removed from the device.

Said guiding means may include at least one longitudinal groove provided on said needle shield or on said housing, and at least one longitudinal rib, provided respectively on said housing or on said needle shield, said rib being engaged in said groove and sliding within said groove when said needle shield is removed from the device.

In another embodiment of the invention, said needle shield is coupled to a deshielder, part of said guiding means being provided on said deshielder.

The device of the invention may further comprise:
first biasing means coupled to said housing for biasing the container toward said insertion position, said first biasing means being in one of a compressed and an extended condition, and
second biasing means coupled to said safety shield for biasing said safety shield toward its second position.

The device of the invention may further comprise:
first retaining means in said housing and arranged to maintain said first biasing means in its compressed condition,
first deactivating means being activatable to release said first retaining means, said first deactivating means being in one of a passive state, in which said first deactivating means cannot cause the release of said first retaining means, and an active state, in which said first deactivating means can cause the release of said first retaining means, wherein movement of said safety shield out of its first position causes passage of said first deactivating means from its passive state to its active state.

The device of the invention is perfectly safe. It is not possible to activate neither the insertion of the needle nor the injection without first applying the device on the injection site. Two steps are needed before starting the operation: first applying the device on the injection site, then exert a manual pressure on the first deactivating means. Exerting a manual pressure on the first deactivating means without applying the device on the injection site beforehand will not activate the insertion since the first deactivating means are then in a passive state.

Moreover, in the injection assistance device of the invention, the safety shield is in its active state well before the end of the injection step.

In a preferred embodiment of the invention, engaging means causes the passage of said safety shield from the passive state to the active state upon completion of insertion of the injection needle at the injection site, and prior to the product being totally expelled from said container through said injection needle.

Therefore, the safety shield is in its active state right at the end of the insertion step, before the injection step actually begins. In this way, even if the patient decides to withdraw the device before the end of the injection, then the safety shield automatically extends over the needle and there is no risk of any accidental needlestick injury for the patient.

The device of the invention may further comprise:
second retaining means provided on at least one of said housing and said safety shield to prevent movement of said safety shield to its second position.

In an embodiment of the invention said second retaining means comprises a flexible tongue and an abutment surface.

The device of the invention may further comprise:
first engaging means capable of releasing said second retaining means thereby enabling movement of said safety shield to its second position under the bias of said second biasing means.

In an embodiment of the invention, said first engaging means comprises an inner ring coupled to the container and comprising a leg cooperating with said flexible tongue so as to disengage said flexible tongue from said abutment surface when the container moves to said insertion position.

In an embodiment of the invention, said first deactivating means is a push button having a distal end, and said device further comprises:

third retaining means, arranged to maintain said push button in its passive state, said third retaining means comprising a radially flexible leg provided on an outer sleeve, said outer sleeve being coupled to said housing, said distal end of said push button being blocked in axial and distal translation by said radially flexible leg,
said safety shield further comprising a tooth that engages said third retaining means when said safety shield is moved out of its first position so as to deflect said radially flexible leg and enable passage of said push button from its passive state to its active state.

The device of the invention may further comprise a plunger rod for causing the piston to move with respect to the container,
said first retaining means comprising a flexible tooth, provided on one of said outer sleeve and said plunger rod, and engaged with a radial stop provided on one of said plunger rod and said outer sleeve,
said push button comprising a tooth capable of cooperating with said flexible tooth so as to disengage said flexible tooth from said radial stop, under manual pressure exerted on said push button in its active state, thereby deactivating said first retaining means and causing the container to move from its initial position to its insertion position.

The device of the invention may further comprise locking means arranged to prevent movement of said inner ring when said first deactivating means is in its passive state, said locking means being able to be unlocked through the movement of said safety shield out of its first position.

In an embodiment of the invention, said first biasing means comprises automatic injection means, arranged in such a way as to cause said plunger rod to move said piston within the container when the container is in said insertion position, thereby causing the product to be automatically expelled from the container without any manual operation from the user.

In an embodiment of the invention, said automatic injection means is disposed around said plunger rod.

In another embodiment of the invention, said automatic injection means is disposed within said plunger rod.

The device of the invention may further comprise injection controlling means to produce an audible indicator when the piston is proximate said distal end of the container and the product is substantially completely expelled from the container thereby informing the user that injection of the product is completed, said injection controlling means producing an audible indicator regardless of whether a user maintains pressure on said first deactivating means.

The device of the invention may further comprise injection controlling means to produce an audible indicator as the product is being expelled from the container, said audible indicator stopping when the piston is proximate said distal end of the container and the product is substantially completely expelled from the container thereby informing the user that injection of the product is completed, said injection controlling means producing an audible indicator regardless of whether a user maintains pressure on said first deactivating means.

In an embodiment of the invention said injection controlling means comprises:
a plunger rod for causing the piston to move with respect to the container,
first biasing means coupled to at least one of said housing and said plunger rod, said first biasing means being in one of a compressed and an extended condition, and means for interacting with said first biasing means to provide an injection status indication to a user of said device.

Preferably, said means for interacting comprises a radial projection in contact with said first biasing means so as to produce an audible indication as said radial projection moves with respect to said biasing means.

In an embodiment of the invention, said first biasing means and said second biasing means each comprise at least a spring.

The device of the invention may further comprise tamper-evidence means removably coupled with said housing to shield said needle prior to use of said device, said tamper-evidence means being in one of a pre-use condition and a post-use condition, said post-use condition preventing re-use of said tamper evidence means with said device.

Alternatively, said post-use condition preferably provides a visual indication that said tamper evidence means has been removed from said device.

In an embodiment of the invention said tamper-evidence means comprises a deshielder coupled to said needle shield, said post-use condition proving an indication that said tamper-evidence means has been removed from said device.

The present invention also relates to a kit for a device for automatic injection of a product into an injection site, the product being carried by a container having an open proximal end and a substantially closed distal end and having a reservoir defined therebetween, and a needle provided at the distal end and in fluid communication with the reservoir to provide an outlet port for the product from the container, and a piston provided in the container and movable with respect with the container, the movement of the piston causing the product to be expelled from the container through the needle, characterized in that said kit comprises:

a housing assembly comprising:
        an upper housing assembly,
        a lower housing assembly, at least one of said upper and said lower housing assembly being adapted to receive part of the container, the container being movable, when received within said at least one of said upper and said lower housing assembly, between an initial position, in which a tip of the needle does not extend beyond a distal end of said lower housing assembly and in which the container is in one of a passive state and an active state, to an insertion position, distally spaced relative to said initial position and in which the tip of the needle extends beyond said distal end of said lower housing assembly, movement of the container out of its first position being prevented when the container is in its passive state, and being permitted when the container is in its active state, and
        means for connecting said upper housing and said lower housing together, and
    a safety shield coupled to one of said upper and said lower housing assembly for movement between a first position and a second position in which the tip of the needle does not extend beyond a distal end of said safety shield, movement of said safety shield out of its first position placing the container in its active state, said safety shield being movable to its second position when the container is in said insertion position, said safety shield being secured against proximal movement when in said second position, and
    a needle shield coupled with one of said upper and said lower housing assembly and covering the needle prior to use of said device, removal of said needle shield being with limited or no rotation of said needle shield.

The kit of the invention may further comprise means for carrying at least one of said upper housing assembly and said lower housing assembly, said carrying means carrying said one of said upper housing assembly and said lower housing assembly in a predetermined orientation.

In accordance with this embodiment of the present invention, an automatic injection device is provided to a pharmaceutical company, for example, in condition for easy assembly and processing in the company's manufacturing processes. The upper and lower housing assemblies are each carried on a tray that provides orientation for the assemblies. In addition, the syringe (i.e., container) may be inserted into the housing assemblies without having to orient the syringe to either of the upper or lower assemblies. In a simple assembly process, the pharmaceutical company fills the syringe, inserts the syringe into one of the upper and lower housing assemblies, and connects the housing assemblies together.

Figures 4, 5:
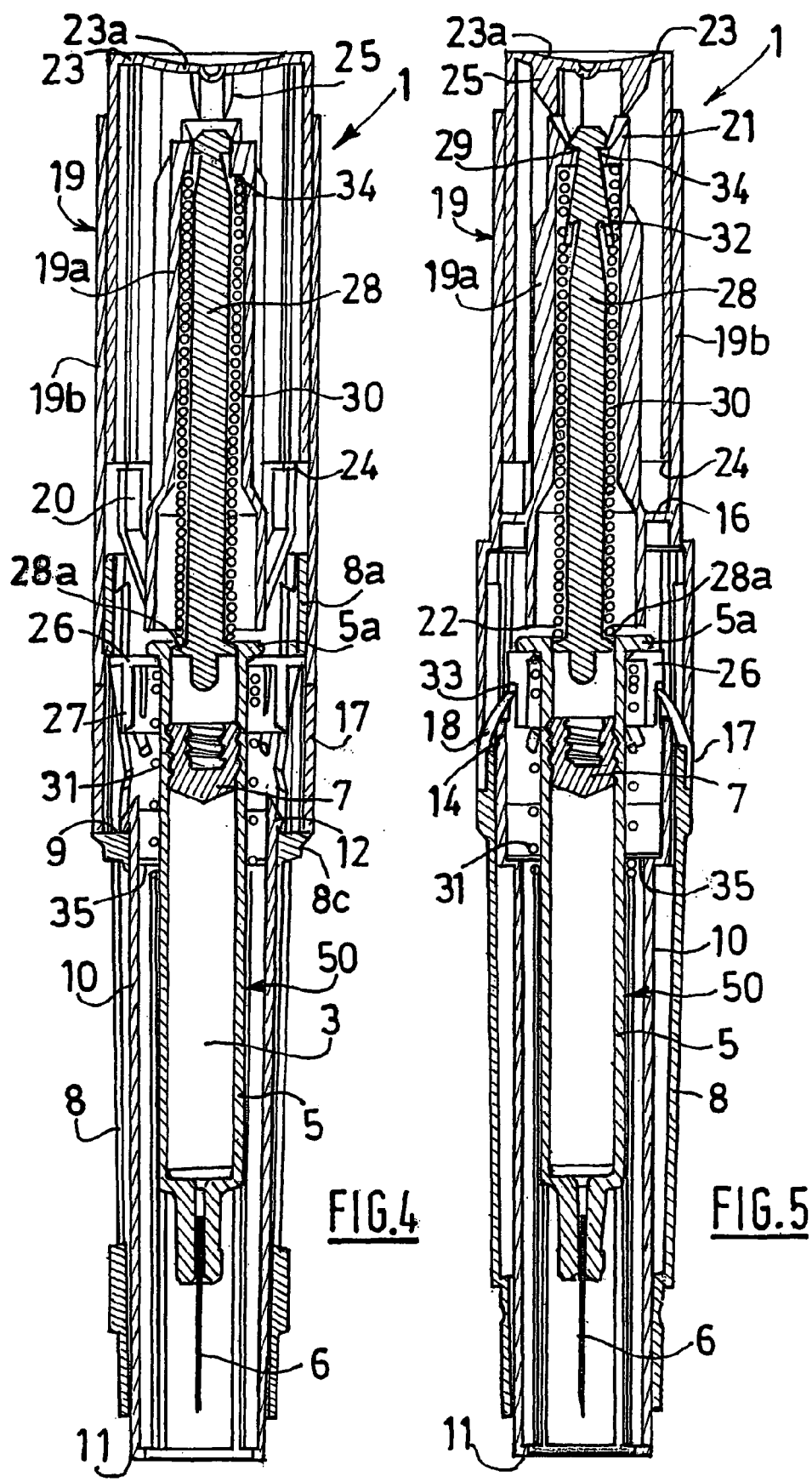
Figures 9, 10:
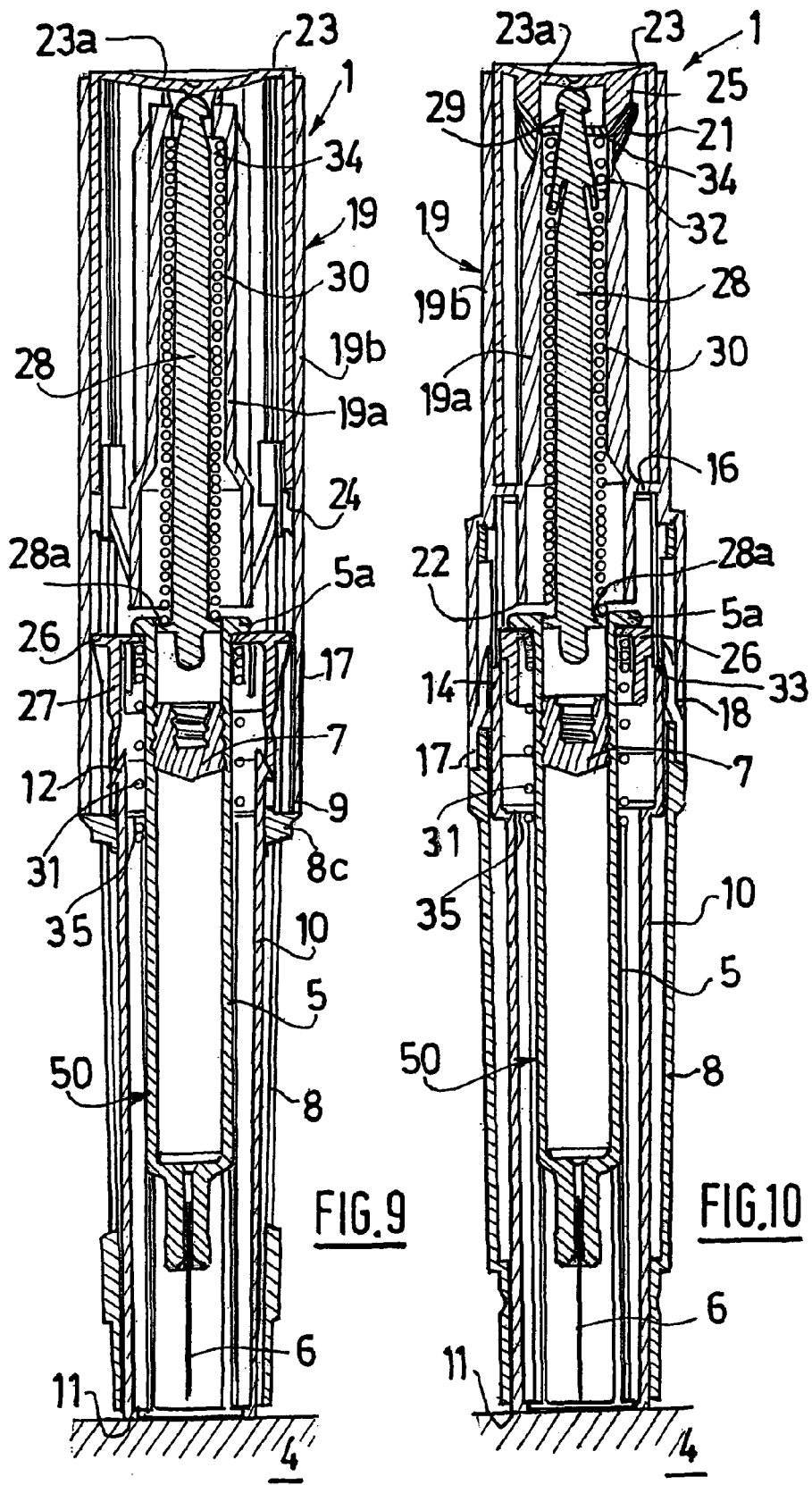
Figure 15:
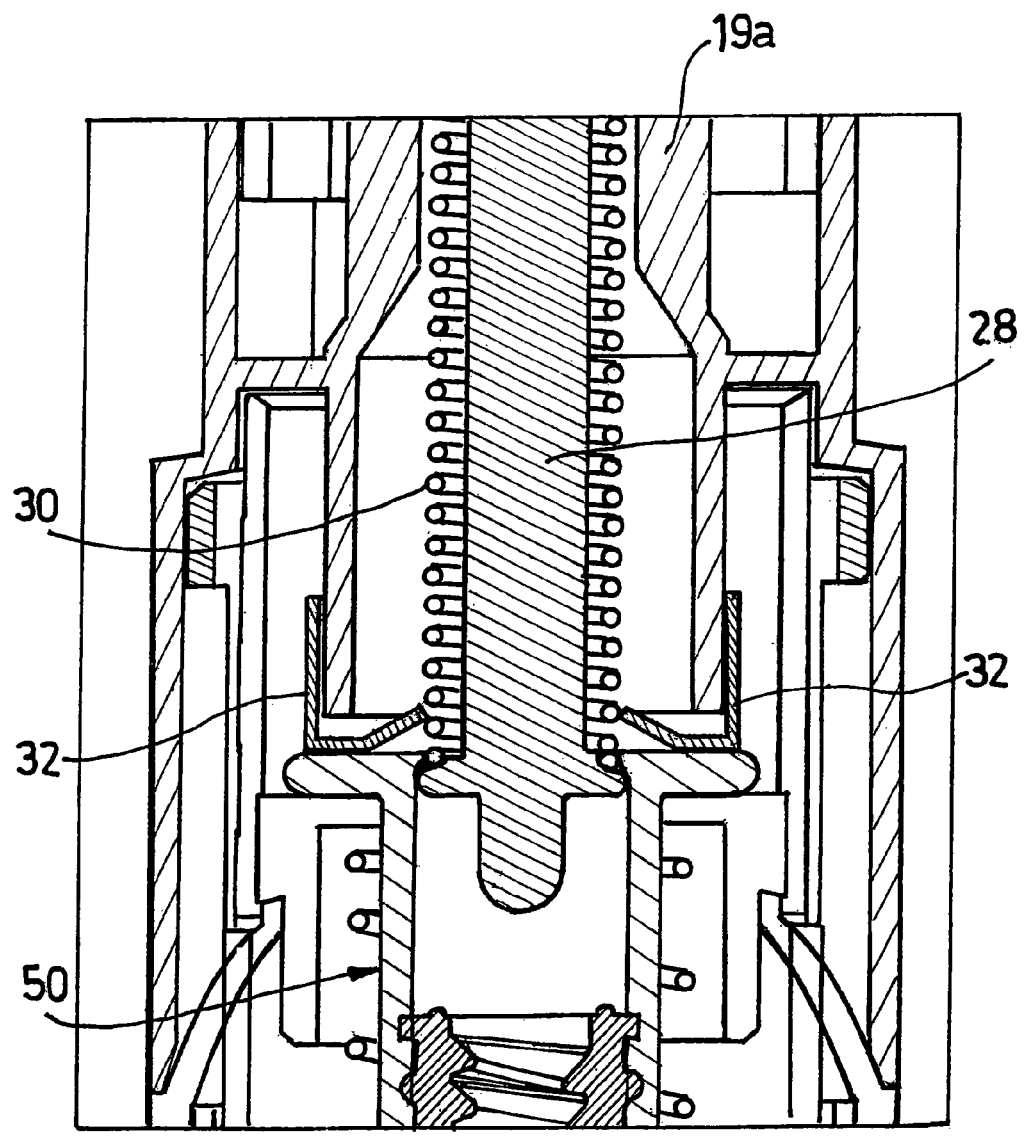
Figure 21:
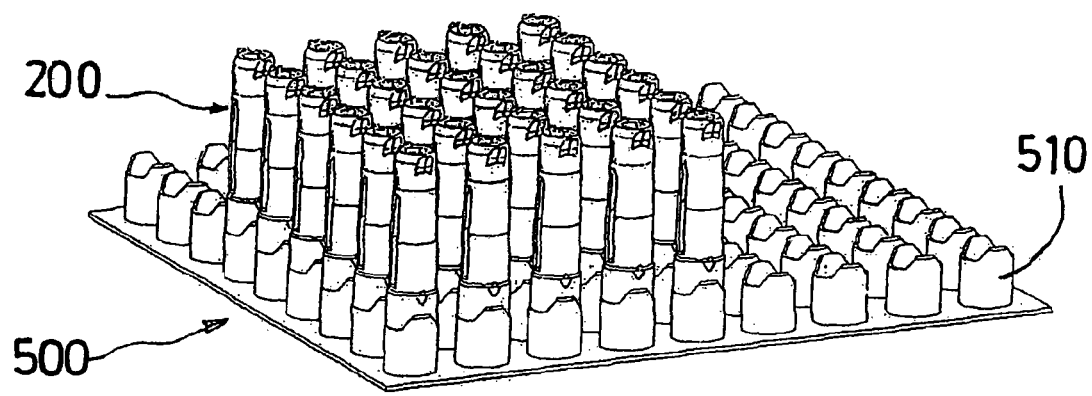
Figure 22:
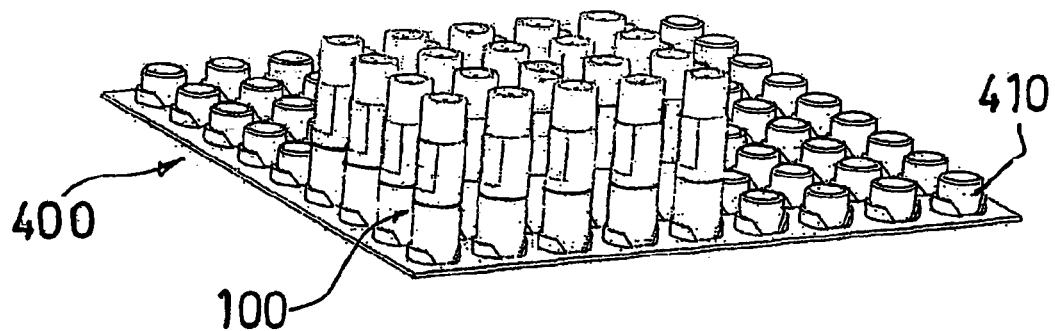
Figure 23:
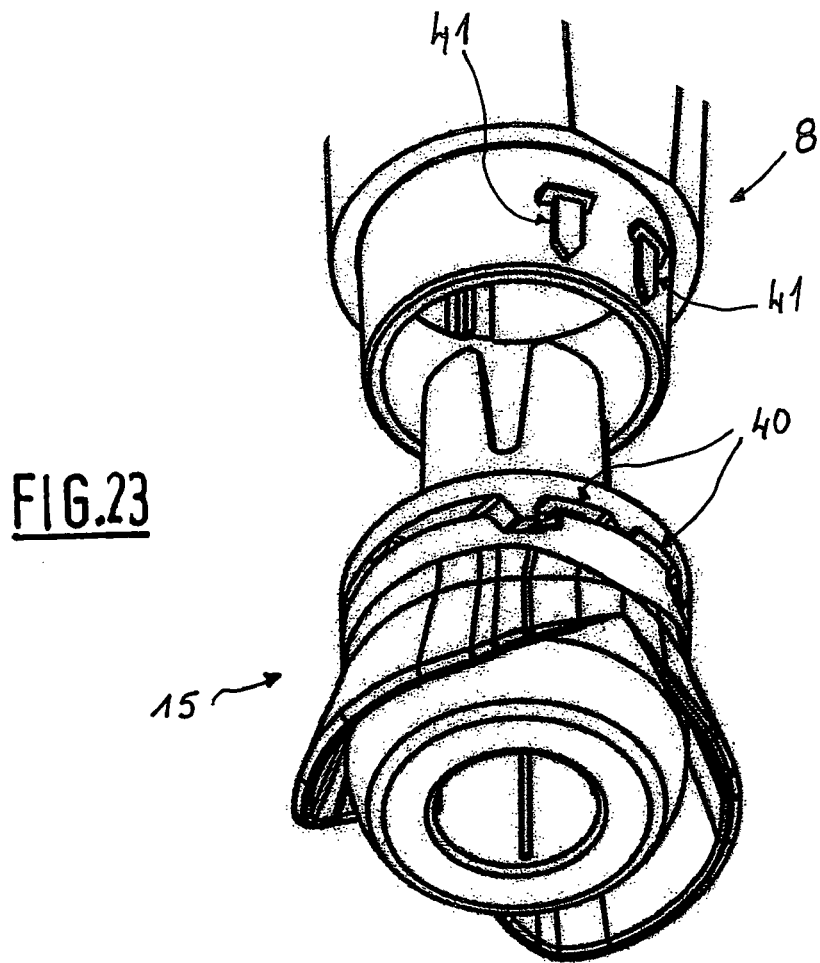
Figure 24:
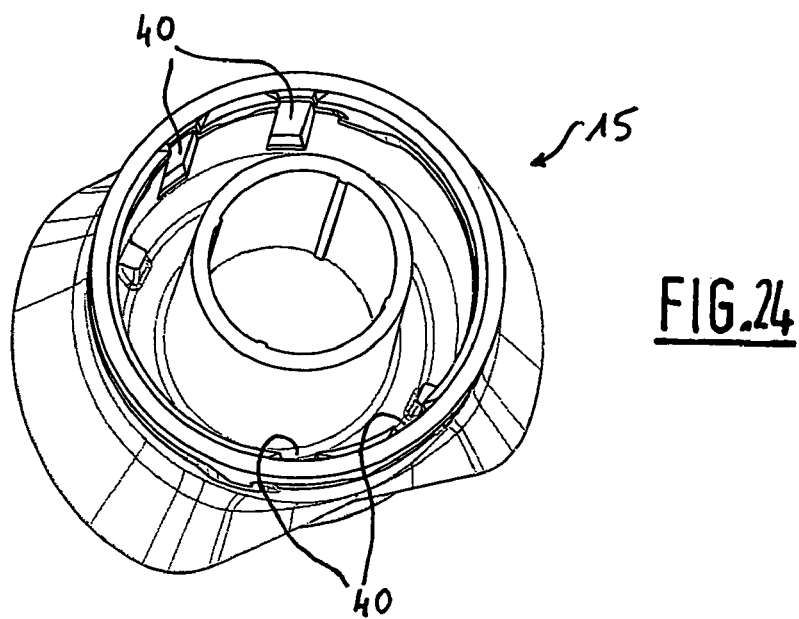

The device of the invention will now be further described in reference to the following description and attached drawings in which:

FIG. 1 is an exploded perspective view of an embodiment of the device of the invention, FIG. 2 is a longitudinal cross section view of the device of FIG. 1, before use, with a needle shield and a deshielder, according to a longitudinal plane comprising the longitudinal axis AA' of the device 1, and passing through the middle of window 8d, FIG. 3 is a longitudinal cross section view, shifted of 90° compared to FIG. 1, FIGS. 4 and 5 are longitudinal cross section views of the device of FIG. 1, respectively corresponding to FIGS. 2 and 3, in the initial position, after removal of the needle shield and the deshielder, FIGS. 6 to 8 are longitudinal cross section views of the device of FIG. 1 with the device placed against a user's skin at an injection site, wherein FIG. 8 corresponds to a longitudinal cross section view shifted of 45° compared to FIG. 6, FIGS. 9 and 10 are longitudinal cross section views of the device of FIG. 1 showing the activation of the first deactivating means, FIGS. 11 and 12 are longitudinal cross section views of the device of FIG. 1 with the container in its insertion position before injection, FIGS. 13 and 14 are longitudinal cross section views of the device of FIG. 1 at the end of the injection step, FIG. 15 shows an alternate embodiment of an indicator for providing an injection status to the user, FIGS. 16 and 17 are longitudinal cross section views of the device of FIG. 1 with the safety shield in the extended position, after removal of the device from the injection site, FIG. 18 shows an alternate embodiment of the device of the present invention with a hollow plunger rod and with the first spring disposed within the plunger rod, FIGS. 19a to 19d show a deshielder in accordance with the present invention that provides a tamper-evidence means to indicate to a user of the device that the deshielder has been removed from the device, FIG. 20 is a perspective view of a kit comprising an upper housing assembly and a lower housing assembly in accordance with the present invention, FIG. 21 is a perspective view of a tray for carrying a plurality of lower housing assemblies in an oriented manner, and FIG. 22 is a perspective view of a tray for carrying a plurality of upper housing assemblies in an oriented manner, FIG. 23 is a perspective view of a deshielder of a device of the invention, said deshielder being coupled to a needle shield, FIG. 24 is a perspective view from the top of the deshielder of FIG. 23.

Referring now to the drawings, the present invention will now be described in detail. FIG. 1 shows an exploded perspective view of a device for automatic injection according to an embodiment of the present invention and generally designated by reference number 1. The inventive device 1 comprises a housing 300 comprised of an upper housing assembly 100 and a lower housing assembly 200 that may be connected to each other by means of a snap-fit connection 110, 210 (see, e.g., FIG. 20), screw-type connection, bayonet connection, or other means of connecting two parts together, in an unreleasable way or not. When the device of the injection is of a single use type, the means for connecting the upper housing assembly 100 to the lower housing assembly 200 are made unreachable to the user. A container 50 such as, for example, a syringe, is received in at least one of the upper and lower housing assemblies 100, 200. Preferably, the container 50 is partially received in each of the upper and lower housing assemblies 100, 200, as discussed in more detail herein. The container 50 has a flange 5a defined at an open proximal end, and an injection needle 6 (see, e.g., FIG. 2) at a substantially closed distal end 5b. Lateral walls 5 extend between the proximal and distal ends and define a reservoir 5c sized and shaped to contain a predetermined amount of a product 3 for injection. The injection needle 6 may be fixed to the distal end 5b, or removable therefrom, as a matter of design choice. The injection needle 6 is in fluid communication with the reservoir 5c and provides an outlet port of the container 50 for the product 3. A needle shield 2 is provided at the distal end of the container 50 to cover and protect the needle 6 before use of the device 1. The needle shield 2 also provides for a sealing means of the distal end of the container 50 before use. A piston 7 is provided in the container 50 and which is movable within the reservoir 5c. Movement of the piston 7 causes the product 3 to be expelled from said container 50 through the injection needle 6 during the injection of the product 3 into the patient.

With reference to FIGS. 1-3, the upper housing assembly 100 of the device 1 of the present invention will now be described in further detail. The upper housing assembly 100 has a generally cylindrically shaped outer sleeve 19 comprised of an inner cylinder 19a and an outer cylinder 19b, the cylinders 19a and 19b being linked to each other by at least a radial wall 16. The distal part of the inner cylinder 19a is provided on its outer wall with at least two flexible legs 20 protruding in the proximal direction and being capable of being radially deflected. The proximal end of the inner cylinder 19a is provided with two flexible teeth 21, capable of being radially deflected, and with an inner radial rim 34.

The upper housing assembly 100 further comprises a push button 23 received in the outer sleeve 19. The proximal end of the push button 23 is closed by a transversal wall 23a which forms a pushing surface for the user to exert a manual pressure on said push button 23. The distal end 24 of the push button 23 is open. The distal face of the transversal wall 23a is provided with two distal teeth 25.

A plunger rod 28 for causing said piston 7 to move with respect to said container 50, as will be explained later, is received within the inner cylinder 19a of said outer sleeve 19 of the upper housing assembly 100. The plunger rod 28 is provided at its distal end with a flange 28a and at its proximal end with a radial stop 29. The plunger rod 28 is provided, in its proximal portion, with two radial projections 32, the function of which will be explained later.

A first spring 30 is provided between said plunger rod 28 and said inner cylinder 19a. The distal end of the spring 30 bears on the flange 28a of the plunger rod 28, and the proximal end of the spring 30 bears on the distal face of the inner radial rim 34 of the inner cylinder 19a. Spring 30 causes displacement of the container 50 within at least one of the upper and lower housing assemblies 100, 200 from an initial position to an injection position, and further causes movement of the piston 7 within the container 50 to cause the product 3 to be expelled therefrom through the injection needle 6.

With continued reference to FIGS. 1-3, the lower housing assembly 200 of the device 1 of the present invention will now be described in further detail. The lower housing assembly 200 comprises a housing 8 which receives, at least partially the container 50. As will appear later, the container 50 is movable relative to said housing 8 between an initial position, in which a tip of the needle 6 does not extend beyond a distal end of the housing 8 (see, e.g., FIG. 4), and an insertion position, distally spaced relative to said initial position and in which the tip of the needle 6 extends beyond the distal end of the housing 8 and is exposed over a predetermined length (see, e.g., FIG. 11).

The housing 8 has a general cylindrical shape and is open at both ends. The housing 8 has a distal part 8b and a proximal part 8a, the diameter of the proximal part 8a being greater than the diameter of the distal part 8b. The proximal part 8a and the distal part 8b of the housing 8 are joined by a radial wall 8c. The proximal surface 9 of the radial wall 8c forms an abutment surface, the function of which will be explained later. The housing 8 comprises two opposite windows 8d in its proximal part 8a.

The lower housing assembly 200 also includes a safety shield 10 that is at least partially received within the housing 8. A proximal part of the safety shield 10 is provided on its outer wall with two opposite flexible tongues 12, capable of being radially deflected. The proximal part of the safety shield 10 is also provided with two opposite first proximal teeth 13 and with two opposite second proximal teeth 14, distally spaced from said first proximal teeth 13. The safety shield 10 is provided, on its inner wall, with a radial rim 35, distally spaced from said flexible tongues 12.

The safety shield 10 is coupled to the housing 8 and is able to move between a first position and a second position in which the tip of the needle does not extend beyond a distal end of the safety shield 10.

The device 1 of the present invention further comprises an inner ring 26 which receives part of the proximal portion of said container 50, the inner diameter of said inner ring 26 being less than the outer diameter of the flange 5a of said container 50 so as to prevent to container 50 from passing completely through the ring 26 when the ring 26 and container 50 are assembled together (see, e.g., FIG. 3). When assembled together, the inner ring 26 and container 50 may move together within the upper and lower housing assemblies 100, 200 as the container 50 is moved from its initial position to its insertion position (discussed in more detail below). The inner ring 26 comprises at least two distal legs 27 and at least two outer radial rims 33, tangentially spaced from said two distal legs 27.

The device 1 of the present invention also comprises an outer ring 17 which receives, at least partially, said inner ring 26. The outer ring 17 is provided on its inner wall with at least two opposite radially flexible tongues 18 that extend in the proximal direction.

A second spring 31 is provided between said container 50 and said inner ring 26. As shown on FIG. 2, the distal end of the second spring 31 bears on the proximal face of the radial rim 35 of the safety shield 10, and the proximal end of said second spring 31 bears on a distal face of said inner ring 26.

The device 1 of the present invention is also provided with a deshielder 15 for removing the needle shield 2. As shown in FIGS. 19a-19d, the deshielder 15 carries the needle shield 2. The deshielder 15 is coupled to the needle shield 2. Prior to use of the device 1, a user removes the deshielder 15, which also removes the needle shield 2.

As shown on FIGS. 23 and 24, the deshielder 15 is provided with longitudinal grooves 40 and the distal region of the housing 8 is provided with longitudinal ribs 41. The grooves 40 and the ribs 41 are aligned with the axis of the device so as to provide a single direction for the removal of the deshielder 15 coupled to the needle shield 2 (not shown), and so as to act as guiding means allowing only a sliding longitudinal translation of the deshielder/needle shield with respect to the housing 8 when said deshielder/needle shield is removed from the device 1. As can be seen from FIG. 23, the distal end of the ribs 41 are reduced so as to facilitate the alignment of the ribs 41 with the grooves 40. Because of the specific features of the deshielder 15, the needle shield 2 can not be rotated before use, and the removal of the needle shield 2 can not be achieved with a rotational movement, thus reducing or eliminating the rotation of the rubber protection in which the needle 6 is embedded before use. This reduces or eliminates the risk of creating rubber particles due to the sharpness of the distal tip of the needle 6. In consequence, there is no generation of particles at the tip of the needle 6 and the quality of the injection to come is not impacted.

In another embodiment of the invention, not shown, the needle shield 2 and/or the deshielder 15 may be equipped with ribs and the housing 8 is provided with grooves, said ribs and said grooves cooperating together to limit or avoid any rotational movement of the needle shield 2 when said needle shield is removed from the device 1.

In an embodiment of the invention, the number of ribs is equal or less than the number of grooves. The number of ribs should be sufficient to lock in rotation the needle shield when attempted to be moved with a rotational movement by hand.

In another embodiment, not shown, the grooves may be enlarged at their extremity, with a chamfer for instance, in order to facilitate said deshielder/needle shield to be assembled onto said housing for industrial purpose and to facilitate the assembly operation.

In one embodiment of the present invention, the deshielder 15 and needle shield 2 provide a way for a user of the device 1 to determine whether the device 1 has been tampered with prior to use. Generally stated, the deshielder 15 and needle shield 2 provide an indication to the user when the deshielder 15 has been removed from the device 1—that is, when it has been removed from the lower housing assembly 200. FIGS. 19b and 19c show, respectively, the deshielder 15 coupled to the device 1 and the deshielder 15 removed from the device 1; the device 1 in FIG. 19c being ready for use.

Once the deshielder 15 that carries the needle shield 2 has been removed, it cannot be placed back onto the device 1, that is onto lower housing assembly 200, without generating a backward shift of the needle shield 2 versus the deshielder 15. The device 1 of the invention may contain sterile drugs and it is important to prove to end users that the container has not been tampered, and that the drug sterility has been maintained until the point of use. The present invention advantageously describes such a feature.

The functioning of the device 1 will now be explained in reference to FIGS. 4-18. Before providing a detailed description of the operation of a device 1 constructed in accordance with the present invention, the following general description of its operation is provided. The inventive device 1 is provided to a user ready-to-use. The container 50 is filled with a predetermined dose of an injectable product 3—preferably a single dose thus providing a one-time use or disposable injection device. Multi-dose or reusable injection devices are also contemplated by, and with the scope and spirit of the present invention. Prior to use, the user removes the deshielder 15 and the needle shield 2, without rotation of said needle shield 2, and places the device 1 against his/her skin at an injection site 4. As the device 1 is pressed against the user's skin, the safety shield 10 is caused to move in the proximal direction and into the housing 8. Due to safety features of the inventive device 1, a user cannot activate the device 1 (i.e., cause the container 50 to move from its initial position to its injection position) until the safety shield 10 is caused to move a predetermined distance in the proximal direction. Indeed, the container 50 is in its passive state as long as the safety shield 10 has not moved out of its first position. With the device 10 pressed against his/her skin (and the safety shield 10 moved out of its first position in the proximal direction), the container 50 adopts its active state, and the user can activate the device 1 and begin an injection by pressing the push button 23. That will cause the container 50 to move from its initial position to its injection position, which also causes the needle 6 to pierce the user's skin. In addition, by pressing the push button 23 once, the inventive device 1 causes the injectable product 3 to automatically be expelled from the container and into the user's skin. While the injection is being made or at the end of the injection process, the device 1 provides an audible indicator to the user of the status of the injection. For example, the device 1 may provide one or more audible clicks as the injection is being made—with the absence of a click indicating an end of the injection. In another example, a single click may indicate the end of the injection process. The audible clicks are made regardless of whether the user maintains pressure on the push button 23. Once the injection is complete, the user removes the device 1 from the injection site and the safety shield 10 is caused to automatically extend from the housing 8 (i.e., lower housing assembly 200) to cover the now-contaminated tip of the needle 6. Advantageously, even if the user removes the device 1 from the injection site 4 before the injection is complete, the safety shield 10 will automatically extend over the tip of the needle. Once the device 1 is removed from the injection site 4 and the shield 10 is extended over the tip of the needle 6, the shield 10 locks in place and cannot thereafter be moved from its locked position in the proximal direction to expose the tip of the needle 6. The used device 1 is thus rendered safe for handling and disposal.

On FIGS. 4 and 5 is shown the device 1 before use, as provided to the user. As shown on FIG. 3, the container 50 is held in its initial position and the first spring 30 is held in a compressed condition by flexible teeth 21 of the inner cylinder 19a being engaged in the radial stop 29 of the plunger rod 28 and the flexible tongues 18 of the outer ring 17 being engaged in the radial rim 33 of the inner ring 26. The inner ring 26 and thus the container 50 are thereby prevented from moving distally. The inner ring 26 is also prevented from moving proximally by the proximal part 8a of the housing 8.

As shown on FIG. 2, the flexible tongues 12 of the safety shield 10 are engaged on the abutment surface 9 of the housing 8. The first spring 30 is in a pressurized or compressed condition, and the second spring 31 is in non-compressed or extended condition.

The flange 5a of the container bears on the inner ring 26. The container 50 is therefore retained in its initial position by the combined actions of the flexible teeth 21 of the inner cylinder 19a, the radial stop 29 of the plunger rod 28 and the inner ring 26, which act as first retaining means of said container 50 in its initial position.

In this position, the needle 6 is protected by the needle shield 2 which is contained within the deshielder 15. The needle 6 and the needle shield 2 are both received within the safety shield 10.

When the user decides to realize the injection, he/she first removes the deshielder 15: by this operation, he/she also removes the needle shield 2, as shown on FIGS. 4 and 5.

In the example shown on FIG. 23, the shape of the deshielder is such that it limits or prevents the needle shield to rotate around the needle. This is an advantage of the present invention as, usually, needle shields are made of rubber or elastomeric material. The sharp needle, embedded into the rubber shield may create a core of rubber if rotated when removed. Then, this rubber core, located into the needle internal diameter may then block the needle and prevent the drug to be injected or may be injected into the patient's skin together with the drug upon activation of the injection device.

As can be seen from FIGS. 4 and 5, after deshielding, the container 50 is still retained in its initial position, and the needle 6 is still protected by the safety shield 10. On these FIGS. 4 and 5, the container 50 is in its passive state.

In the position shown on FIGS. 2 to 5, the push button 23 is also in a passive state such that depression by a user on the pushing surface 23a will not cause the device 1 to make an injection. Although the push button 23 is movable in the distal direction when the button 23 is in the passive state, it cannot cause activation of the device 1 because a distal end 24 of the push button 23 comes in contact with the proximal end of the flexible legs 20 of the inner cylinder 19a. The push button 23 is therefore stopped and the device 1 can not be triggered or activated. The push button 23 and the container 50 are both in their passive state. The device 1 of the invention is therefore particularly safe, as it cannot be triggered through a single action (i.e., only by pressing on the push button 23).

The triggering of the device 1 of the invention requires at least two steps. In a first step, the push button 23, which acts as a deactivating means of the first retaining means of the first spring 30 in its compressed condition and of the container 50 in its initial position, must previously be caused to pass from a passive state, in which the exercise of a manual pressure by the user on said push button 23 does not cause the release of said first retaining means, to an active state, in which the exercise of said manual pressure does cause the release of said first retaining means. As discussed in more detail below, movement of the safety shield 10 out of its first position causes the push button 23, and in consequence the container 50, to move from their passive state to their active state.

This first step is shown on FIGS. 6 and 7. In this first step, the user applies the device 1 on the injection site 4 by means of the bearing surface 11 of the safety shield 10. He/she then exerts a distal force on the housing 8 thereby causing the safety shield 10 to move relative to said housing 8 from a first position, namely a rest position, shown on FIGS. 4 and 5, for example, to an intermediate position, namely a bearing position, shown on FIGS. 6 and 7—the bearing position being proximally spaced relative to said rest position. During this movement, the first proximal teeth 13 of the safety shield 10 contact the flexible legs 20 of the inner cylinder 19a and cause the flexible legs 20 to deflect radially towards the center of the device 1, as shown on FIG. 8. Once deflected as just described, the flexible legs 20 do not opposingly face the distal end 24 of the push button 23 and said push button 23 is now in its active state.

Movement of the safety shield 10 from its rest position to its bearing position also places the container 50 in its active state. During such movement of the safety shield 10, the second proximal teeth 14 of the safety shield 10 contact the radially flexible tongues 18 of the outer ring 17 and cause the flexible tongues 18 to deflect radially thereby disengaging them from the radial rim 33 of the inner ring 26, in which they were engaged. Upon such deflection, the container 50 is placed in its active state and able to move to its injection position. However, movement of the container 50 to its injection position does not occur upon the release or deflection of the flexible tongues 18 because the inner ring 26 and container 50 are biased in the proximal direction by the second spring 31. Moreover, the inner ring 26 is also blocked in the proximal direction by the proximal part 8a of said housing 8. As a consequence, during this first step, although the container 50 is able to move in the distal direction, it does not and is retained in its initial position. Actually, the container 50 is retained in its initial position, but now in its active state, so that movement of the container out of its initial position may now be permitted, although only upon pressing of the push button 23.

In an alternative embodiment of the invention, the push button 23 is not coupled to said plunger rod 28 when the push button 23 is in its passive state. The push button 23 is then allowed to move in its passive state but it is prevented to have any action with the plunger rod 28. After application of the device 1 on the injection site 4, the safety shield 10, or any other engaging means, causes the plunger rod 28 to be coupled to the push button 23 which is then placed in its active state.

The push button 23 being now in its active state, the user can, in a second step, trigger the device 1 to start the automatic injection. The activation of the push button 23 is shown on FIGS. 9 and 10. The user exerts a manual pressure on the pushing surface 23a of the push button 23: the push button 23, which is no more stopped by the flexible legs 20, moves distally, thereby causing the distal movement of the teeth 25 of the push button 23. During this movement, the teeth 25 come in contact with the flexible teeth 21 of the inner cylinder 19a and cause said flexible teeth 21 to deflect radially and outwardly, as shown on FIG. 10.

The flexible teeth 21 are now disengaged from the radial stop 29 of the plunger rod 28 and the first spring 30 is now free to move from its compressed condition to an extended condition. The first spring 30 expands and causes the plunger rod 28, which is coupled to said container 50, to move in the distal direction. Because of the previous disengagement of the flexible tongues 18 from the radial rim 33 of the inner ring 26, both the inner ring 26 and the container 50 are now free to move distally, i.e. the container 50 may move to its injection position. The first spring 30 therefore pushes distally the plunger rod 28, the container 50 and the ring 26 as the container is caused to move to its injection position.

Movement of the container 50 to its injection position also causes the needle 6 to pierce the user's skin at the injection site 4. The depth of insertion of the needle 6 into the user' skin at the injection site 4 is controlled by the interaction between the distal legs 27 of said inner ring 26 and the abutment surface 9 of the housing 8, as shown on FIGS. 11 and 12. When the end of distal legs 27 engage abutment surface 9, movement of the container 50 in the distal direction, and thus, injection of the needle 6 into the user's skin, is stopped. The needle 6 is now inserted into the injection site 4 over a predetermined length, said predetermined length being controlled by the engagement of said distal legs 27 on said abutment surface 9, as shown on FIGS. 11 and 12.

In another embodiment of the invention, the insertion depth of the needle 6 could be controlled by the engagement of said distal legs 27 on an abutment surface provided on the safety shield 10. Alternatively, the insertion depth could be variable, and/or controlled. While it may not be desirous to enable a user to vary the injection depth, such control may be desirable in the hands of a pharmaceutical company or supplier of the injection device 1 of the present invention. For example, different injection depths may be desired for different pharmaceutical compounds (i.e., injectable products). Depending upon the product 3 provided in the container 50, it may be necessary for the pharmaceutical company or other supply of the inventive device 1 to set the injection depth for each different compound. This may be accomplished by enabling the pharmaceutical company to control the spatial relationship between the distal legs 27 and abutment surface 9—that relationship controlling the injection depth of the needle 6.

During this insertion of the needle 6, the inner ring 26 has moved distally and its distal legs 27 have come in contact with the flexible tongues 12 of the safety shield 10, causing the flexible tongues 12 to be deflected radially and inwardly, as shown on FIG. 11. During this same distal movement of the inner ring 26, the second spring 31 has been caused to compress and has reached a pressurized or compressed condition, as shown on FIG. 11. Yet, the distal end of said second spring 31 bears on the radial rim 35 of said safety shield 10 which is maintained against the injection site 4 by the distal pressure exerted by the user on the device 1 and said second spring 31 is therefore not free to expand.

It can be seen from FIG. 11 that because of the now deflected state of the flexible tongues 12, the abutment surface 9 no longer be an obstacle to the distal movement of said flexible tongues 12. Therefore, in the insertion position of the needle as shown on FIGS. 11 and 12, removal of the device 1 from the injection site 4 by the user at this stage of the operation would cause the safety shield 10 to be moved distally to its second position by the second spring 31 to cover and protect the needle 6. When in the second position, the safety shield 10 is locked against proximal movement thereby preventing unintended access to the contaminated needle 6.

As noted above, once the container 50 is in its insertion position, the safety shield 10 is movable to its second position. In consequence, in this position, the safety shield 10 automatically extends to its second position when a user removes the device 1 from the injection site 4 any time after the container 50 has been moved to its injection position. The device 1 of the invention is therefore particularly safe and it prevents accidental needlestick injuries even in case said device 1 is removed from the injection site 4 before the injection of the product is actually completed.

At the end of the insertion step, the force of the first spring 30, which continues its expansion, overcomes the friction of the flange 28a of the plunger rod 28 against the inner wall of the container 50, and the distal end of the plunger rod 28 comes in contact with the piston 7 with which it becomes coupled at least in the distal direction.

The first spring 30 still continues its expansion, overcomes the stiction of the piston 7 and the piston 7 is caused to move distally, realizing the injection of the product 3, as shown on FIGS. 13 and 14. The injection is therefore completed automatically without any manual operation from the user.

The radial projections 32 provided on the plunger rod 28 are in contact with said first spring 30 but they do not prevent the first spring 30 from extending in the distal direction. In consequence, each time the radial projections 32 touch a part of the first spring 30, for instance each time they touch a spire of the spring, they produce a sound. Of course, when the piston 7 is proximate to the distal end of the container 50 and the product 3 is substantially completely expelled from said container 50, the first spring 30 is stopped and by way of consequence, the sound also stops. The user is thereby informed that the injection is proceeding, and also when the injection is complete.

The first spring 30 and the radial projections 32 therefore constitute injection controlling means that produce an audible indicator as the product 3 is being expelled from the container 50, said audible indicator stopping when the piston 7 is proximate said distal end of the container 50 and the product 3 is substantially completely expelled from the container 50 thereby informing the user that injection of the product is completed.

In an alternative embodiment shown in FIG. 15, the radial projections 32 are provided as part of the inner cylinder 19a.

The radial projections 32 therefore constitute good controlling means of the completion of the injection. The user knows when the product is being injected, and also when substantially all the product is injected, thereby preventing removal of the device 1 from the injection site 4 before the desire dose of the product 3 is injected.

When the injection is completed, the user removes the device 1 from the injection site 4, as shown in FIGS. 16 and 17. As noted above, removal of the device 1 from the injection site 4 any time after the container 50 is in its injection position will result in movement of the safety shield 10 to its second position in which it is locked over the needle 6 (i.e., the tip of the needle 6 does not extend beyond a distal end of the safety shield 10). Movement of the safety shield 10 is effected by the second spring 31 as it returns to an extended condition upon removal of the device 1 from the injection site 4.

Movement of the safety shield 10 out of its second position is prevented by cooperating structural elements provided on the safety shield 10 and the inner ring 26, for example.

In an alternative embodiment of the invention shown in FIG. 18, the plunger rod 28 is hollow and the first spring 30 is received within the hollow plunger rod 28. By providing an option of locating the first spring 30 either inside or outside of the plunger rod 28, the present invention enables springs of different force to be used in the inventive device 1 depending upon the particular requirements of the device 1. For example, the needle 6 internal diameter may vary, or the viscosity of drugs contained in the reservoir 50 may also vary. These factors may increase significantly the injection duration, which can be very uncomfortable for the patient. To limit the injection duration in such cases, different spring forces may be required to accommodate different container configurations, and the present invention provides means for addressing such different configurations.

In the embodiment shown in FIG. 18, the audible indicator may comprise one or more projections provided on an inner wall of the hollow plunger rod 28.

Alternatively, it is possible to produce an audible indicator at the end of the injection: in such a case, for instance, the first spring presents a variable diameter that engages a projection 32 only at or near the end of the injection.

Referring next to FIGS. 20-22, an alternate embodiment of the present invention will now be described in further detail. In this embodiment, a kit 300 comprised of an upper housing assembly 100 and a lower housing assembly 200. Details of each of the upper and lower housing assemblies 100, 200 have been described in detail above, and need not be described further. The kit 300 may be provided to a pharmaceutical company, for example, together with a syringe (i.e., a container), for easy processing and assembly by the pharmaceutical company. The syringe may be provided as part of the kit 300, but it need not be—the kit 300 comprising the upper and lower housing assemblies 100, 200. The upper and lower housing assemblies 100, 200 are connected to each other by connecting means 110, 210 provided on each of the assemblies 100, 200. Connecting means 110, 210 may be a snap-fit connection, screw-type connection, bayonet connection, or other means of connecting two parts together.

Each of the upper and lower housing assemblies 100, 200 may be provided on a tray 400, 500, each having a plurality of receptacles 410, 510 that each receives one of an upper and a lower housing assembly 100, 200. The receptacles 410, 510 provide orientation for the housing assemblies 100, 200, further facilitating processing and assembly by the pharmaceutical company. Thus, a pharmaceutical company, for example, may receive the kit 300 and place the kit 300 directly into their manufacturing process for filling (of the syringe) and assembly of the upper and lower housing assemblies 100, 200 with the syringe. Due to the orientation provided by the receptacles 410, 510, assembly of the syringe with the upper and lower housing assemblies 100, 200 is simple, quick, and easily fits within a pharmaceutical company's existing manufacturing processes.

The device of the invention is very easy to use and very safe. In particular, with the injection device and the kit of the invention, the generation of contaminating particles or dust in the area of the needle shield at the time the needle shield is removed from the injection device is avoided.

The injection device of the invention also allows automatic injection of a product to be performed by a patient without any risk of needlestick injury, before, during and after use. In particular, the safety shield of the device of the invention is in its active state right at the end of the insertion step, before the injection step actually begins. In this way, even if the patient decides to withdraw the device before the end of the injection, then the safety shield automatically extends over the needle. Moreover, the device of the invention allows the user to be informed of the compete injection of the product: this is particularly important when very precise doses of product must be injected. It is also a real benefit for the patient to be precisely informed of the end of the injection, since the end of the injection step is usually long with self-injectors, due to the fact that the spring that realizes the automatic injection slows its course down after a certain time.

The invention claimed is:

1. A device for automatic injection of a product into an injection site, the product being carried by a container having an open proximal end and a substantially closed distal end and having a reservoir defined therebetween, and a needle provided at the distal end and in fluid communication with the reservoir to provide an outlet port for the product from the container, and a piston provided in the container and movable with respect to the container, the movement of the piston causing the product to be expelled from the container through the needle, said device comprising:
   a housing for the container, the container being movable relative to said housing between an initial position, in which a tip of the needle does not extend beyond a distal end of said housing and in which the container is in one of a passive state and an active state, to an insertion position, distally spaced relative to said initial position and in which the tip of the needle extends beyond said distal end of said housing, movement of the container out of its initial position being prevented when the container is in its passive state, and being permitted when the container is in its active state,
   a safety shield coupled to said housing for movement between a first position and a second position in which the tip of the needle does not extend beyond a distal end of said safety shield, movement of said safety shield out of its first position placing the container in its active state, said safety shield being movable to its second position when the container is in said insertion position, said safety shield being secured against proximal movement when in said second position, and
   a needle shield coupled with said housing and covering the needle prior to use of said device, removal of said needle shield from the device being with limited or no rotation of said needle shield.

2. A device according to claim 1, wherein said needle shield and said housing are provided with guiding means designed to allow the longitudinal translation of the needle shield with respect to said housing while preventing its rotation, when said needle shield is removed from the device.

3. A device according to claim 2, wherein said guiding means include at least one longitudinal groove provided on said needle shield or on said housing, and at least one longitudinal rib, provided respectively on said housing or on said needle shield, said rib being engaged in said groove and sliding within said groove when said needle shield is removed from the device.

4. A device according to claim 2, wherein said needle shield is coupled to a deshielder, and part of said guiding means is provided on said deshielder.

5. A device according to claim 1, wherein said device further comprises:
   first biasing means coupled to said housing for biasing the container toward said insertion position, said first biasing means being in one of a compressed and an extended condition, and
   second biasing means coupled to said safety shield for biasing said safety shield toward its second position.

6. A device according to claim 5 wherein said device further comprises:
   first retaining means in said housing and arranged to maintain said first biasing means in its compressed condition,
   first deactivating means being activatable to release said first retaining means, said first deactivating means being in one of a passive state, in which said first deactivating means cannot cause the release of said first retaining means, and an active state in which said first deactivating means can cause the release of said first retaining means, wherein movement of said safety shield out of its first position causes passage of said first deactivating means from its passive state to its active state.

7. A device according to claim 6, wherein said device further comprises second retaining means provided on at least one of said housing and said safety shield to prevent movement of said safety shield to its second position.

8. A device according to claim 7, wherein said second retaining means comprises a flexible tongue and an abutment surface.

9. A device according to claim 7, wherein said device further comprises:
   first engaging means capable of releasing said second retaining means thereby enabling movement of said safety shield to its second position under the bias of said second biasing means.

10. A device according to claim 9, wherein said first engaging means comprises an inner ring coupled to the container, and a leg cooperating with said flexible tongue so as to disengage said flexible tongue from said abutment surface when the container moves to said insertion position.

11. A device according to claim 6, wherein said first deactivating means is a push button having a distal end, and in that said device further comprises: third retaining means, arranged to maintain said push button in its passive state, said third retaining means comprising a radially flexible leg provided on an outer sleeve, said outer sleeve being coupled to said housing, said distal end of said push button being blocked in axial and distal translation by said radially flexible leg, said safety shield further comprising a tooth that engages said third retaining means when said safety shield is moved out of its first position so as to deflect said radially flexible leg and enable passage of said push button from its passive state to its active state.

12. A device according to claim 11, wherein said device further comprises a plunger rod for causing the piston to move with respect to the container,
said first retaining means comprising a flexible tooth, provided on one of said outer sleeve and said plunger rod, and engaged with a radial stop provided on one of said plunger rod and said outer sleeve,
said push button comprising a tooth capable of cooperating with said flexible tooth so as to disengage said flexible tooth from said radial stop, under manual pressure exerted on said push button in its active state, thereby deactivating said first retaining means and causing the container to move from its initial position to its insertion position.

13. A device according to claim 10, wherein said device further comprises locking means arranged to prevent movement of said inner ring when said first deactivating means is in its passive state, said locking means being able to be unlocked through the movement of said safety shield out of its first position.

14. A device according to claim 11, wherein said first biasing means comprises automatic injection means, arranged in such a way as to cause said plunger rod to move said piston within the container when the container is in said insertion position, thereby causing the product to be automatically expelled from the container without any manual operation from the user.

15. A device according to claim 14, wherein said automatic injection means is disposed around said plunger rod.

16. A device according to claim 14, wherein said automatic injection means is disposed within said plunger rod.

17. A device according to claim 1, wherein said device further comprises injection controlling means to produce an audible indicator when the piston is proximate said distal end of the container and the product is substantially completely expelled from the container thereby informing the user that injection of the product is completed, said injection controlling means producing an audible indicator regardless of whether a user maintains pressure on said first deactivating means.

18. A device according to claim 17, wherein said injection controlling means comprises,
a plunger rod for causing the piston to move with respect to the container,
first biasing means coupled to at least one of said housing and said plunger rod, said first biasing means being in one of a compressed and an extended condition, and
means for interacting with said first biasing means to provide an injection status indication to a user of said device.

19. A device according to claim 18, wherein said means for interacting comprises a radial projection in contact with said first biasing means so as to produce an audible indication as said radial projection moves with respect to said biasing means.

20. A device according to claim 5, wherein said first biasing means and said second biasing means each comprise at least a spring.

21. A device according to claim 1, wherein said device further comprises tamper-evidence means removably coupled with said housing to shield said needle prior to use of said device, said tamper-evidence means being in one of a pre-use condition and a post-use condition; said post-use condition preventing re-use of said tamper evidence means with said device.

22. A device according to claim 21, wherein said device further comprises tamper-evidence means removably coupled with said housing to shield said needle prior to use of said device, said tamper-evidence means being in one of a pre-use condition and a post-use condition, said post-use condition providing a visual indication that said tamper evidence means has been removed from said device.

23. A device according to claim 21, wherein said tamper-evidence means comprises a deshielder coupled to said needle shield, said post-use condition proving an indication that said temper-evidence means has been removed from said device.

24. A kit for a device for automatic injection of a product into an injection site, the product being carried by a container having an open proximal end and a substantially closed distal end and having a reservoir defined therebetween, and a needle provided at the distal end and in fluid communication with the reservoir to provide an outlet port for the product from the container, and a piston provided in the container and movable with respect to the container, the movement of the piston causing the product to be expelled from the container through the needle, wherein said kit comprises:
a housing assembly comprising:
an upper housing assembly, a lower housing assembly, at least one of said upper and said lower housing assembly being adapted to receive part of the container, the container being movable, when received within said at least one of said upper and said lower housing assembly, between an initial position, in which a tip of the needle does not extend beyond a distal end of said lower housing assembly and in which the container is in one of a passive state and an active state, to an insertion position, distally spaced relative to said initial position and in which the tip of the needle extends beyond said distal end of said lower housing assembly, movement of the container out of its first position being prevented when the container is in its passive state, and being permitted when the container is in its active state;
means for connecting said upper housing and said lower housing together, and
a safety shield coupled to one of said upper and said lower housing assembly for movement between a first position and a second position in which the tip of the needle does not extend beyond a distal end of said safety shield, movement of said safety shield out of its first position placing the container in its active state, said safety shield being movable to its second position when the container is in said insertion position, said safety shield being secured against proximal movement when in said second position, and a needle shield coupled with one of said upper and said lower housing assembly and covering the needle prior to use of said device, removal of said needle shield being with limited or no rotation of said needle shield.

25. A kit according to claim 24, wherein said kit further comprises means for carrying at least one of said upper housing assembly and said lower housing assembly, said carrying means carrying said one of said upper housing assembly and said lower housing assembly in a predetermined orientation.

* * * * *